United States Patent
Gudmundsdottir et al.

(10) Patent No.: US 12,370,066 B2
(45) Date of Patent: Jul. 29, 2025

(54) DEVICE AND METHOD FOR RESISTIVE TORQUE CONTROL IN A MAGNETORHEOLOGICAL ACTUATOR USING A RECOVERY PULSE

(71) Applicant: Össur Iceland ehf, Reykjavik (IS)

(72) Inventors: Anna Gudmundsdottir, Reykjavik (IS); Gunnar Omar Lillie Magnusson, Reykjavik (IS); Maarten Ganseij, Reykjavik (IS)

(73) Assignee: Össur Iceland ehf, Reykjavik (IS)

( * ) Notice: Subject to any disclaimer, the term of this patent is extended or adjusted under 35 U.S.C. 154(b) by 0 days.

(21) Appl. No.: 18/058,155

(22) Filed: Nov. 22, 2022

(65) Prior Publication Data

US 2023/0165692 A1    Jun. 1, 2023

Related U.S. Application Data (60) Provisional application No. 63/264,692, filed on Nov. 30, 2021.

(51) Int. Cl.
*A61F 2/64* (2006.01)
*A61F 2/68* (2006.01)
*A61F 2/70* (2006.01)

(52) U.S. Cl.
CPC ............ *A61F 2/64* (2013.01); *A61F 2/70* (2013.01); *A61F 2002/6818* (2013.01); *A61F 2002/6863* (2013.01); *A61F 2002/701* (2013.01)

(58) Field of Classification Search
CPC ...... A61F 2/64; A61F 2/70; A61F 2002/6818; A61F 2002/6863; A61F 2002/701
See application file for complete search history.

(56) References Cited

U.S. PATENT DOCUMENTS

| | | | | |
|---|---|---|---|---|
| 2006/0085082 A1* | 4/2006 | Asgeirsson | ............... | A61F 2/70 623/44 |
| 2010/0185124 A1* | 7/2010 | Bisbee, III | ................ | A61F 2/70 600/595 |
| 2010/0312363 A1* | 12/2010 | Herr | .......................... | A61F 2/70 623/39 |

FOREIGN PATENT DOCUMENTS

CN    111449813 A    7/2020

OTHER PUBLICATIONS

International Search Report and Written Opinion in PCT Application No. IB2022/061306 as mailed on Feb. 17, 2023 in 30 pages.

* cited by examiner

*Primary Examiner* — Jerrah Edwards
*Assistant Examiner* — Maximilian Tobias Spencer
(74) *Attorney, Agent, or Firm* — Knobbe Martens Olson & Bear LLP (57) ABSTRACT

A prosthetic or orthotic device has an elongate frame that houses electronics and an actuator rotatably mounted to the frame. The actuator can rotate in an anterior-posterior direction about a medial-lateral axis and includes magnetorheological (MR) fluid and a coil operable to selectively apply a magnetic field to the MR fluid to vary its viscosity and thereby vary a torsional resistance of the actuator about the medial-lateral axis. Circuitry controls an amplitude and a direction of a current applied to the coil. The circuitry can switch a direction of current passing through the coil, and to apply a reverse direction current pulse to the coil to reduce a time period over which a resistive torque of the actuator decreases to a baseline resistance amount.

13 Claims, 8 Drawing Sheets

DEVICE AND METHOD FOR RESISTIVE TORQUE CONTROL IN A MAGNETORHEOLOGICAL ACTUATOR USING A RECOVERY PULSE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure relates to a device and method for achieving resistive torque control in a magnetorheological (MR) actuator.

Description of the Related Art

The majority of advanced lower-limb prosthetic devices deployed on lower-limb amputees use a microprocessor-controlled braking device. The braking device's technology and implementation vary significantly, but all provide a certain level of resistance to motion under load, which is leveraged to support the lower-limb amputee while standing on the prosthetic limb. Additionally, where the lower-limb prosthetic device is a knee, the braking device is typically controlled to allow the knee to move freely when the prosthetic limb is in swing phase, hence replicating typical lower limb kinematics observed during gait activities.

Common hydraulic technologies in lower-limb prosthetic devices use valves to provide damping or braking of the device by controlling and regulating the flow of hydraulic fluid. Such hydraulic technologies have a high capacity for quick transition between braking and non-braking states due to the limited displacement required by these components to significantly affect the flow properties, and in turn the hydraulic actuator behaviour. However, one disadvantage of these hydraulic technologies is that they present a rather high restriction to motion, even with the valves fully open, due to the need to move the hydraulic fluid around when the actuator is moving. While these systems are well suited to generating braking forces by creating restriction for the fluid to move through, they present significant inertia and damping when it is required to rapidly move the actuator around under low resistance levels.

SUMMARY

In accordance with one aspect of the disclosure, a limb support device (e.g., prosthetic device, orthotic device) is provided having a braking technology that performs properly in view of the requirements associated with supporting gait activities commonly observed in daily living. The braking technology allows for fast transitions between the braking and non-braking states, as well as presents limited restriction to motion in its non-braking state.

In accordance with another aspect of the disclosure, a controllable braking system is provided that uses a magnetorheological (MR) fluid and its properties to change apparent viscosity when subjected to a magnetic field. In one implementation, the controllable braking system is implemented in a rotary actuator that makes use of shear forces to generate the controllable braking force, which also enables the creation of an actuator with very low restriction to motion when the braking system is not activated, as the fluid itself does not need to move when the actuator is moving. The only force required to move the actuator when the braking system is not activated is the viscous friction between the fluid and the friction elements of the actuator.

While presenting minimal residual braking torque when the braking system is in a non-activated state, MR-actuators rely on the magnetic field and the changes in the properties of the MR fluid for the braking to take place. Apart from electromechanical components used to build small scale controllable hydraulic valves, the MR systems have a reduced bandwidth. Onset of the braking torque requires the magnetic particles present in the MR fluid to move and align under the influence of the magnetic field, which is a relatively slow process. This disclosure demonstrates that the magnetic circuit and overall drive circuit can be advantageously designed to achieve a sufficiently rapid response time from the actuator (e.g., between braking and non-braking states) in view of the gait tasks at hand and user expectations. Additionally, the magnetic field generation strategy disclosed herein can advantageously aid in providing a fast transition between braking and non-braking states, as simply removing the magnetic field will not provide optimal resistive torque fall time and can become a hard limitation for the widespread use of the technology. In accordance with one aspect of the disclosure, instead of simply stopping the current from circulating in the magnetic coil and waiting for the MR fluid particles to slowly lose their cohesion and resulting braking force in an MR-actuator powered lower-limb prosthetic or orthotic device, a method of accelerating the reduction of the residual braking torque is implemented to achieve an overall higher controllable bandwidth for a given actuator design.

In accordance with another aspect of the disclosure, a prosthetic or orthotic device using MR actuator technology is provided. The device has a control system for controlling the amount of braking torque generated by the MR actuator. Aspects of the disclosure also include methods for controlling braking torque in MR actuators.

MR actuators are controllable brakes or dampers, in which a MR fluid is subject to a varying magnetic field, causing a change in its fluid properties, namely the apparent viscosity, which in turn affects the resistive or braking torque generated by the actuator.

A MR actuator braking torque control system forcefully reduces the residual magnetism in the actuator when reducing or removing the braking torque, thereby increasing its overall bandwidth. Faster fall time of the residual braking torque following deactivation of the brake is achieved by driving the magnetic coil current in the opposite direction for a short duration of time. Removing the residual magnetism from the MR actuator allows for faster transition between a high amplitude braking state and a non-braking state, which in turn allows the user to transition from stance phase to swing phase faster. Certain locomotion activities, such as descending stairs, are particularly demanding on the lower-limb actuator's capacity to quickly transition from stance phase to swing phase, which enables increased device performance when operated by a lower-limb amputee. In another implementation, the MR actuator braking torque control system can operate to allow for faster transition between a relatively higher amplitude braking state and a relatively lower amplitude braking state by driving the magnetic coil current in the opposite direction as discussed herein.

In accordance with another aspect of the disclosure, a prosthetic or orthotic device is provided. The prosthetic or orthotic device comprises an elongate frame configured to house electronics. The prosthetic or orthotic device also comprises an actuator movably coupled to the elongate frame. The actuator is configured to rotate in an anterior-posterior direction about a medial-lateral axis, the actuator comprising a magnetorheological (MR) fluid and a coil operable to selectively apply a magnetic field to the MR fluid in order to vary its viscosity and thereby vary a torsional resistance of the actuator about the medial-lateral axis. The prosthetic or orthotic device also comprises circuitry configured to control an amplitude and a direction of a current applied to the coil. The circuitry is configured to switch a direction of current passing through the coil, and to apply a reverse direction current pulse to the coil to reduce a time period over which a resistive torque of the actuator in a braking state decreases to a baseline resistance amount of the actuator in a non-braking state.

In accordance with another aspect of the disclosure, a prosthetic or orthotic device is provided. The prosthetic or orthotic device comprises an elongate frame configured to house electronics. The prosthetic or orthotic device also comprises an actuator movably coupled to the elongate frame. The actuator is configured to rotate in an anterior-posterior direction about a medial-lateral axis, the actuator comprising a magnetorheological (MR) fluid and a coil operable to selectively apply a magnetic field to the MR fluid to vary its viscosity and thereby vary a torsional resistance of the actuator about the medial-lateral axis. The prosthetic or orthotic device also comprises means for actively reducing a residual magnetism in the actuator when reducing or removing the torsional resistance of the actuator.

DETAILED DESCRIPTION

Lower-limb support devices (e.g., prosthetic devices, orthotic devices), such as prosthetic knees, have to support a wide variety of tasks in variable environments and a variety of use cases. An actuator of such lower-limb support devices associated with a particular joint advantageously can provide both static and dynamic levels of performance associated with the load and timing requirements of a given task to support the complete range of performance required by human locomotion.

One requirement for high activity systems is to be able to manage the stance to swing transition efficiently. Unlike the swing to stance transition, stance to swing transition cannot be pre-empted and having a rather accurate synchronization of the device actuator behavior can minimize possible impacts on the user's gait smoothness, balance or need to use non-physiological strategies in order to circumvent the system limitations.

Different actuator technologies will present different time constants, some of them being faster than others, and some of them being more symmetrical in the capacity to generate torque quickly and stop generating torque quickly.

For example, in MR actuators, significant delays can be observed in removing the resistive actuator torque following a high resistance state due to the need to break the magnetic links between the iron particles in the MR fluid, over a fairly large volume. As a comparison, typical electrical motors do not present this specific behaviour, the generated torque being rather directly coupled with current circulating in the windings.

However, supporting locomotion tasks like stairs descent on an advanced prosthetic knee using a shear-type MR damper requires the ability to change the actuator resistive torque level from almost maximum amplitude to a very low level, effectively close to null, in a very short period of time to allow the knee swing phase flexion to take place immediately when the user's weight is removed from the prosthetic leg. Due to the inherent risks related to ambulating down flights of stairs on a prosthetic knee, there is a need for both ensuring user safety and providing robust performance to make the swing phase cycle sufficiently fast, which in turn requires that the actuator be able to quickly reach a low resistive torque state. Additionally, the actuator sizing must account for a wide range of users, including heavy and highly active users who require a maximum actuator resistive torque level, which in some cases increases the actuator time constant and goes against the general intent of ensuring a fast swing cycle when operating in stairs descent.

In one embodiment, actuator bandwidth is optimized by forcing the resistive torque to fall at a faster rate than what would be obtained by simply stopping driving current in the magnetic coil, by advantageously driving the magnetic coil current in the opposite direction for a short amount of time and with a significant amplitude, such that the resulting actuator state shows negligible residual resistive torque.

The timing, amplitude, and duration of the opposite current pulse each have an effect on properly minimizing the resulting actuator resistive torque in a timely manner. Too early of a timing for applying the opposite current pulse will cause the knee to buckle under load, as the user's weight would not have been removed from the prosthetic limb, and the actuator resistance will suddenly drop. Too late of a timing for applying the opposite current pulse will fail at minimizing the swing cycle duration and limit the benefits of the method on the overall system's performance. Amplitude and duration are rather coupled in their effects, even if the whole point of the method tends to minimize the duration in all cases since minimizing the swing cycle duration is preferred. Similarly, sufficient amplitude is preferred since it enables obtaining the desired effect in a faster manner, which also leads to a shorter minimum duration. At the same time, attention must be directed in not using a pulse of too high an amplitude or too long a duration, as the resulting effect would actually be to increase the actuator resistive torque by magnetizing the MR fluid in the opposite direction. In practical terms, the pulse duration should be shorter than the actuator resistive torque rise time to avoid building up torque in the opposite direction. The recovery pulse described herein has a magnitude and period that advantageously approximates the level of torque present in the actuator in order to reduce the resistive torque fall time.

Figure 1:
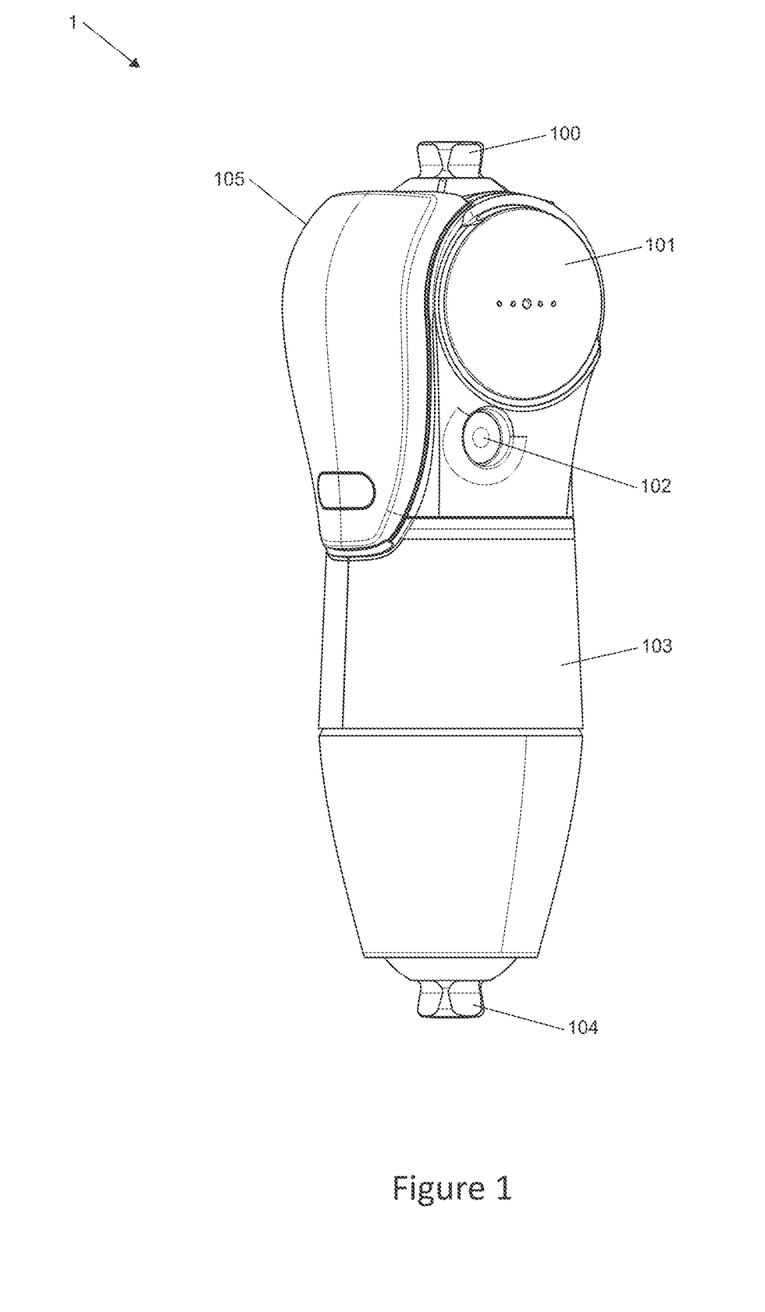
FIG. 1 is a perspective schematic view of a prosthetic knee design using a shear-type MR rotary actuator.

FIG. 1 shows an embodiment of a microprocessor-controlled knee prosthetic device 1 where a shear-type rotary MR actuator is used. This embodiment is a modular component targeted at being assembled with other modular components to create a complete prosthetic leg. Proximal connector 100 is used to structurally connect the knee prosthetic device with the residual limb attachment system (not shown). The knee prosthetic device embodiment is non-specific to the type of residual limb attachment system. Socket systems relying on vacuum or mechanical constraints, or osseo-integration adapters are examples of possible interface solutions. The prosthetic knee integrates the rotary shear-type MR actuator 101 in the knee rotation axis area and allows the thigh mounted segment and proximal connector 100 to rotate with respect to the shank segment 103. The shank segment 103 can house the electronic components and battery required to implement the control electronics, actuator driver, on-board sensors and other various support systems that need to be protected from the environment and possible impact with objects. Mechanical lock actuator 102 allows locking of the motion between the thigh and shank segments of the prosthetic knee. The shank segment 103 is structurally connected to the distal connector 104, which allows connection of the distal modules of the prosthetic leg assembly, for example a shank pylon, as well as the foot and ankle modules. Knee pad 105 is mounted at the front of the MR actuator 101 and the upper shank section 103 in view of providing protection to the components when the device is used for kneeling or similar uses.

Figure 2:
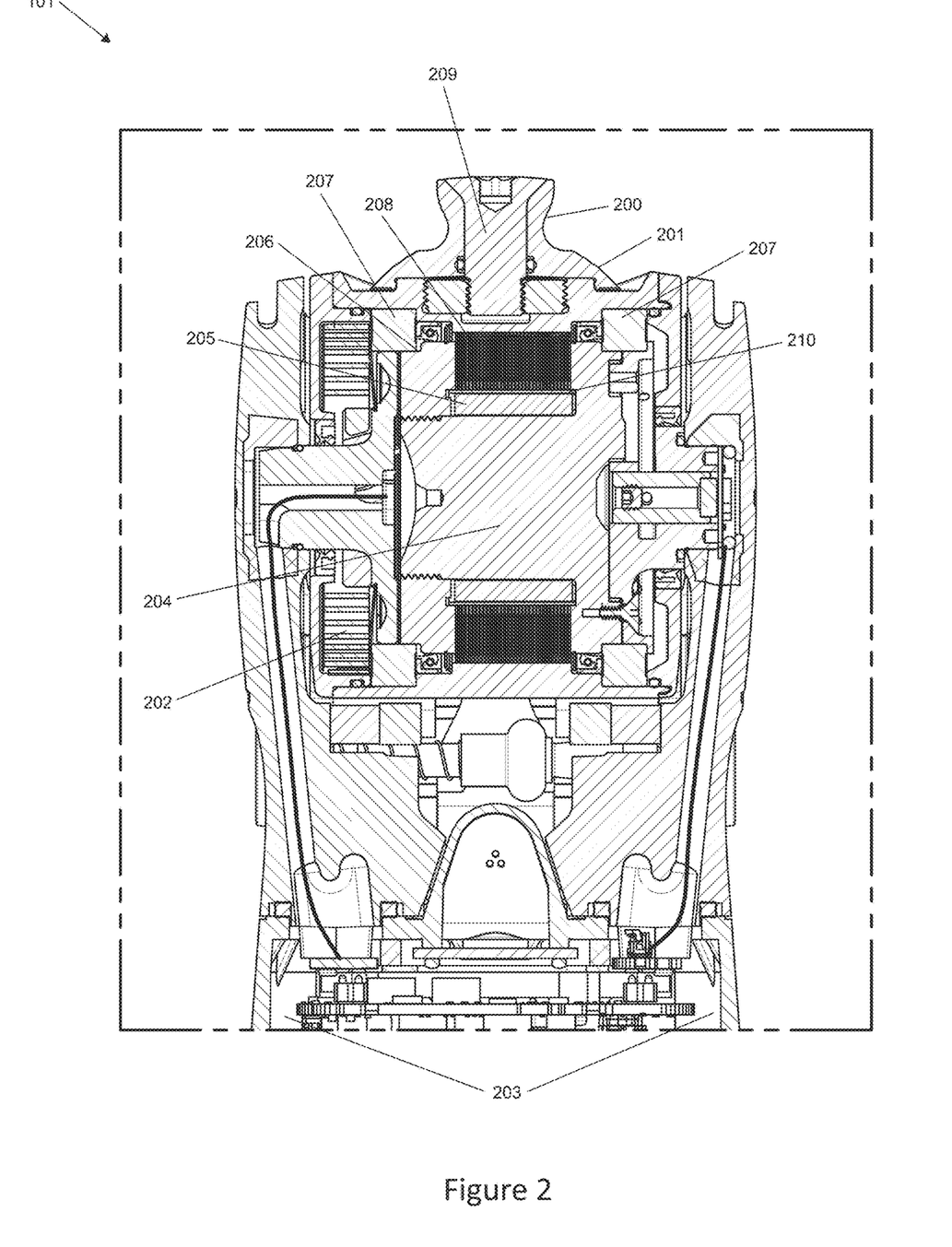
FIG. 2 is a schematic cross-sectional view of a shear-type MR rotary actuator where the high-bandwidth control of the braking torque is achieved.

A cross-sectional view of a knee-axis mounted shear-type MR actuator 101 is detailed in FIG. 2. Proximal connector 200 is connected to the outer spline 201, which in turn can rotate with respect to the knee axis and the structural supports 203 using the bearings 207. Extension spring 202 is operationally connected between the outer spline 201 and the structural supports 203, allowing to bias the joint towards full extension, meaning that the shank and thigh segment of the prosthetic knee will be forced into a full extended knee configuration by the extension spring 202. Proximal connector 200 also integrates the actuator filling plug 209, which can be removed to fill the actuator cavity with MR fluid. The actuator cavity can have a rectangular section revolved around the knee axis, where evenly spaced-out blades manufactured out of a magnetic material 208 are alternatively connected to the thigh segment through the outer spline 201 or the shank segment through the inner spline 210 and the core sides 206. The MR fluid fills in the gaps between the evenly spaced-out blades. The inner spline 210, assembled to the core sides 206 and the core rod 204 create an annular region around the knee axis of, for example, rectangular cross-section, which is filed with the magnetic coil 205.

When current circulates in the magnetic coil 205, a magnetic field is created and induced in the core rod 204, the core side 206 and through the actuator cavity. Based on the magnetic field intensity across the actuator cavity, the MR fluid will change viscosity and increase resistance to motion between the blade sets 208. Conversely, when the current is removed, the magnetic field disappears and the fluid viscosity returns to its original state, allowing the blade sets 208 to move relative to each other with limited resistance to motion. The current direction in the magnetic coil is irrelevant, but for better performance regular direction changes are performed to prevent magnetic field build up.

Figure 3:
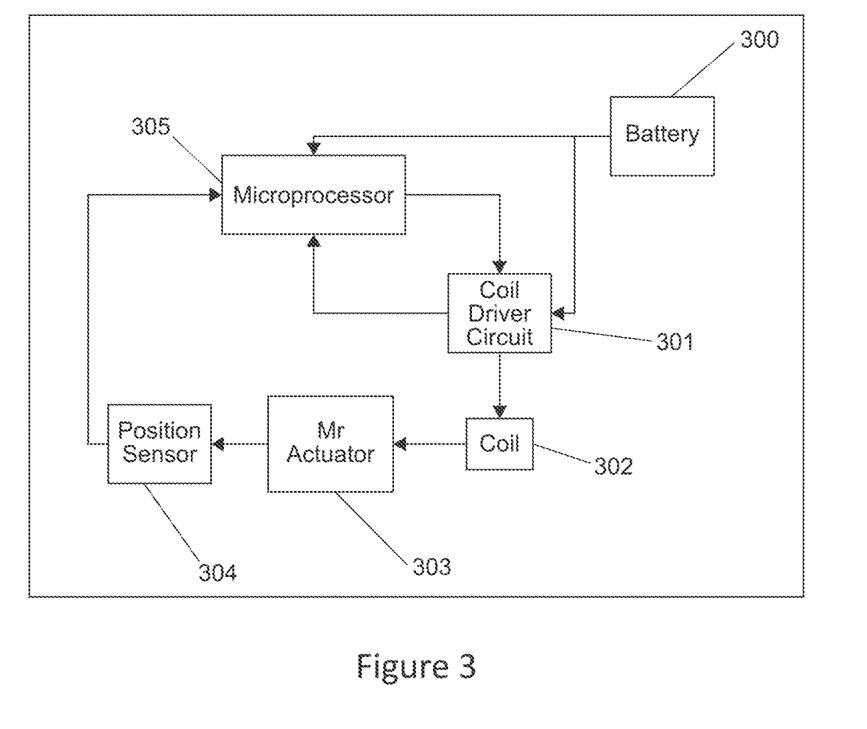
FIG. 3 is a block diagram of a control system for a shear-type MR rotary actuator.

FIG. 3 presents a block diagram of an arrangement of main components for controlling braking torque in a shear-type MR actuator, such as a shear-type MR actuator in a prosthetic knee. A battery 300 is integrated in the control system design to power the microprocessor 305, associated sensors and housekeeping functions, and other electronic components. The battery 300 also supplies power to the magnetic coil 302 through the coil driver circuit 301 to create a magnetic field in the MR actuator 303 and change the braking torque amplitude in the actuator. Microprocessor 305 is in operational communication with the coil driver circuit 301, commanding the current level and direction of current circulating through the coil, while at the same time reading out the actual current level present in the coil. Closed-loop current control is established from the operational connection of the microprocessor 305 and the coil driver circuit 301. Outer loop actuator control is implemented through the addition of the position sensor 304 which allows measuring the actuator reaction when submitted to external perturbations or loads from the user's residual limb. Again, the microprocessor 305 is used to interface the position sensor 304 and implement a digital regulation loop, where velocity and position signals are compared to predefined set-points and used to calculate the amount of current to drive the magnetic coil 302 with.

Figure 4A:
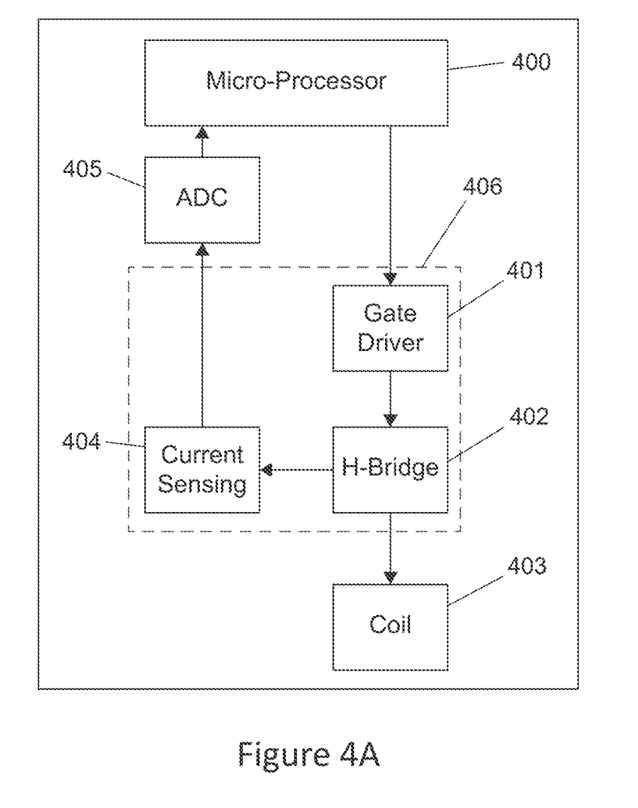
FIG. 4A is a block diagram representation of the actuator drive circuit associated with the shear-type MR rotary actuator.

FIG. 4A further details an embodiment of a MR actuator drive circuit. The microprocessor 400 is in operational communication with the gate driver 401, which is used to interface the switching components provided in the H-bridge circuit 402. The gate driver provides a hardware abstraction layer for the microprocessor, by directly handling the logic functions associated with the H-bridge circuit 402, as well as the basic safety function to ensure proper operation and performance of the H-bridge circuit 402. The magnetic coil 403 is, in one example, directly connected to the H-bridge output, which controls the magnetic coil current amplitude and direction. One particular non-limitative embodiment for controlling the H-bridge output is to use a pulse width modulation driving scheme, under which the H-bridge switching components are turned on and off at high frequency, while the ON duty cycle duration is modulated in order to adjust the resulting average current in the magnetic coil. Current regulation is enabled by a current sensing element 404. The current sensing element 404 may be added to the circuit as a stand-alone element or integrated with the H-bridge circuit 402. The current sensing element 404 is interfaced by the microprocessor 400 which converts the sensing element 404 output into a value that can be compared with the desired set-point in a closed loop control scheme.

Figure 4B:
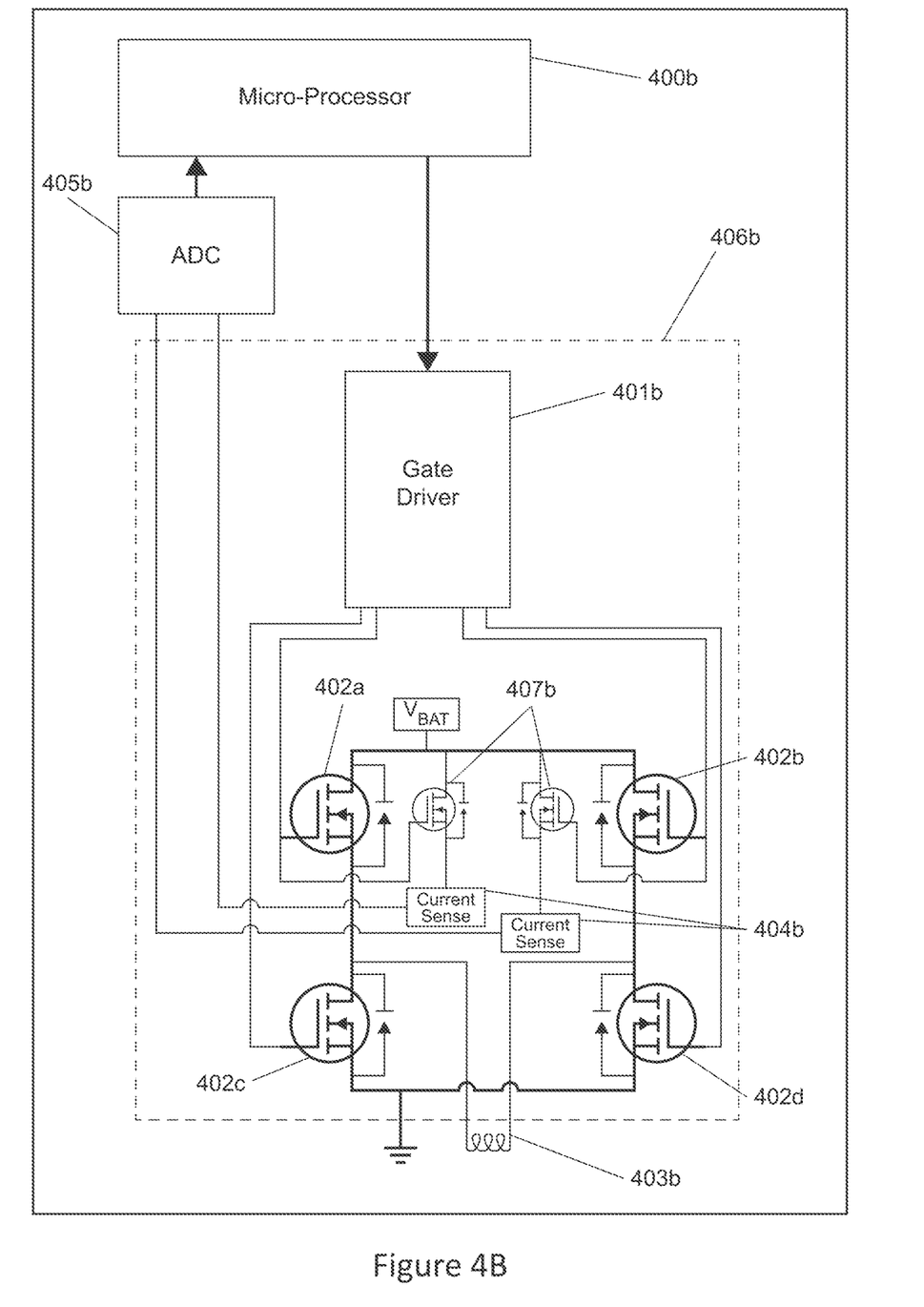
FIG. 4B is a schematic representation of the actuator drive circuit associated with the shear-type MR rotary actuator, including the H-Bridge coil driver.

FIG. 4B further details FIG. 4A by providing a detailed description of the actuator H-bridge coil driver and current sensing blocks presented in FIG. 4A. Microprocessor 400b and gate driver 401b are equivalent to the 400 and 401 blocks of FIG. 4A. H-bridge block 402 from FIG. 4A is detailed through its constituent mosfets 402a, 402b, 402c, and 402d and their connection to the magnetic coil 403b. Individual mosfets are switched by the gate driver 401b to control the current path in the magnetic coil, as well as the amplitude of the current circulating in it. Direction of current circulating in the magnetic coil 403b is selected by the high side mosfet 402a or 402b that is placed in conduction by the gate driver 401b. It is to be noted that the half-bridge composed of a high-side and a low-side mosfet (402a and 402c, and 402b and 402d) are never placed in conduction at the same time, as this would cause a short circuit between the positive supply and the system ground known as shoot-through. Magnetic coil 403b supply circuit is always closed by placing the low-side mosfet 402c or 402d in conduction on the opposite half-bridge of the high-side mosfet 402a or 402b that is placed in conduction. For example, in one coil current driving configuration, high-side mosfet 402a and low-side mosfet 402d are placed in conduction simultaneously while mosfet 402c and 402b are left open, causing the current to circulate in the coil from left to right. In another coil driving configuration, high-side mosfet 402b and low-side mosfet 402c are placed in conduction simultaneously while mosfet 402a and 402d are left open, causing the current to circulate in the coil from right to left. Changing the high-side and low-side mosfet use to connect the magnetic coil 403b effectively allows exchanging the magnetic coil 403b connection between battery supply and ground, which in turn inverts the direction of current flow.

Amplitude of the current circulating at any moment in the magnetic coil 403b is controlled through the functional interaction of the microcontroller 400b, the gate driver 401b and the current sense circuit 404b. Measurement of the current circulating in the magnetic coil 403b is generated by components 407b, which are mirroring the current circulating in the high-side mosfets 402a and 402b. The current mirroring function is provided as part of the chip used to implement the block represented under 406b, which is one non-specific embodiment allowing the implementation of the method herein disclosed. Current measurement issued from components 404b are fed to the analog to digital converter 405b, which in turn is in functional communication with the microprocessor 400b.

Figure 5:
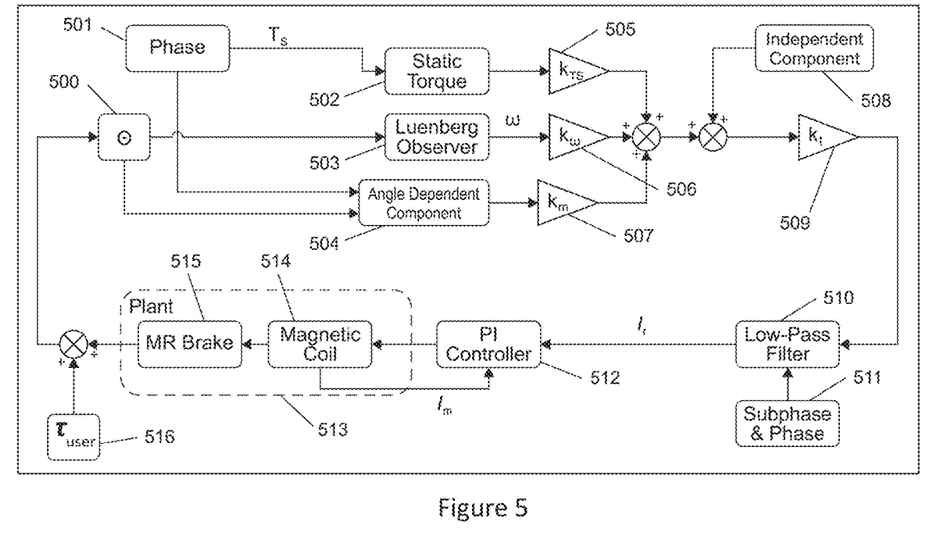
FIG. 5 is a block diagram of a high-level actuator torque control scheme associated with a shear-type MR rotary actuator.

The digitally converted current-equivalent measurement is then fed in a closed-loop control scheme, which proceeds to compare the measured current value with the set-point or desired current, which is issued from the higher-level actuator control scheme, such as presented on FIG. 5. Proportional or proportional and integral gains are applied to the measured error and a new current command is generated. The generated current command is converted into direct commands for the mosfet's ON-time duty cycle. As the mosfets are driven in a pulse-width modulation, the current command is converted directly as a proportion of the full duty cycle (or ON time), which in fact defines the average current to be held over the period where the current command is applied. Pulse width modulation signals issued from the microcontroller or microprocessor 400b are fed to the gate driver 401b, which implements the circuitry to ensure timely and accurate transition of the mosfet conduction state, which advantageously aids in minimizing losses and preventing any damage to the components arising from their operation.

The capacities and properties of the coil driving circuit using a H-bridge will be leveraged in the implementation of the inventive step herein disclosed. It is to be noted that to achieve proper implementation of a recovery pulse to reduce braking torque fall time and satisfactory performance, the H-bridge is advantageously designed in such a way as to ensure that it is possible to change the current direction fast enough and for duration of time relevant with the magnetic circuit characteristics.

FIG. 5 illustrates a high-level actuator torque control scheme block diagram, which operates over the coil driver loop presented in FIGS. 4A and 4B. The actuator control scheme is implemented as a digital controller in the microprocessor 400, 400b outlined previously and is aimed at managing the MR actuator behavior and responses to optimally support locomotion tasks the user is trying to complete. The MR actuator itself is represented by the plant 513, which is further broken down into magnetic coil 514 and MR brake 515 blocks. The knee prosthetic as a whole is also subject to interaction with the user and the environment, which is represented as a perturbation torque 516. The combination of the perturbation torque 516 with the knee prosthetic and actuator components 513 is the target of the control scheme herein presented, as it represents the overall device response when used.

MR brake 515 provides a controlled amount of resistance to motion based on the magnetic field strength going through the MR fluid. Magnetic field is induced by the magnetic coil 514 depending on the amount of current circulating in the magnetic coil. While MR brake 515 resistance is generated in open loop, the magnetic coil is controlled in closed loop, through regulation of the current, which is performed through a digital Proportional-Integral (PI) controller 512, implemented in either the device embedded microprocessor (e.g., microprocessor 400, 400b) or any other digital processing platform available on the device. PI controller 512 compares the current measured in the magnetic coil ("Im") with the current set-point requested from the high-level actuator control loop ("Ir") to determine how to adjust the pulse width modulation parameters to ensure that the measured current Im matches the requested current Ir.

The resulting combination of the MR actuator resistance to motion, user interaction, and perturbation torques from the user and the environment results in the prosthetic knee joint instantaneous position O 500. Actuator position data 500 is fed into a Luenberg Observer 503 to generate an actuator rotational velocity estimate $@$, which is then fed through the velocity gain $k_\omega$ 506. Velocity term of the control loop is the main continuous control part, as a strong correlation exists between actuator velocity and the actuator resistance level required for the user to successfully complete the locomotion task undertaken. To support the specific actuator behaviors, three discrete terms are added to the control loop and are executed based on specific conditions associated with the device usage. The Static Torque 502 block consists in a feedforward term which is fed through a static torque gain $k_{TS}$ 505, which allows forcing a minimum actuator resistive torque when the actuator velocity is null or below a certain threshold, while the knee prosthetic enters the stance phase following user weight transfer over the prosthetic foot. While the characteristics of the static torque profile can be varied based on the exact nature of the locomotion task, a general characteristic where amplitude is observed to decay in time following triggering is considered optimum as it provides a better loading response to the user weight without preventing the user from quickly moving the knee if desired. In a situation where the actuator velocity would be sufficiently high, the velocity arm of the controller (Luenberg Observer 503 and velocity gain 506) would provide enough responsiveness and there is not a hard need to add the contribution of the static torque 502 component. Static torque triggering is driven by the Phase detection engine 501, which is part of the intent management section of the control system of FIGS. 5A and 5B.

Figure 5A:
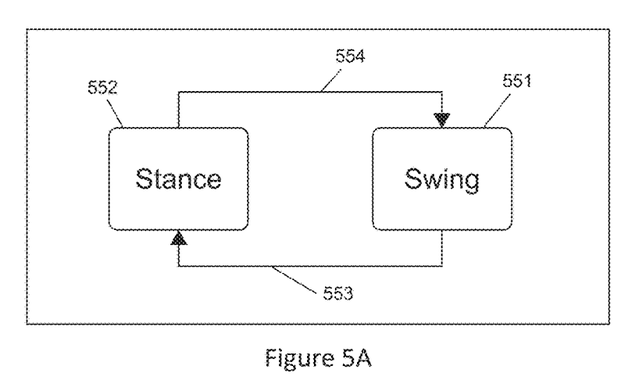
FIG. 5A is a block diagram of a phase state machine.

FIG. 5A provides details on a Phase state machine (e.g., the Phase detection engine 501 in FIG. 5). From a human locomotion perspective, two phases are to be considered and are fundamental to the control of the lower-limb prosthetic device. The state machine is built around having a specific state for each phase. Swing Phase state 551 is characterized by the fact that the prosthetic limb is not carrying the user weight or no contact between the prosthetic limb and the ground is observed during this state. For practical consideration, this state will be entered when a predefined set of conditions are met, typically coming from the Stance Phase state 552. Stance Phase state 552 is effectively the counterpart of the Swing Phase state 551 and is characterized by the prosthetic lower limb being in contact with the ground or user body weight being carried by the prosthetic limb. Similar to the Swing Phase state 551, Stance Phase state 552 will be entered when a predefined set of conditions are met, typically coming from the swing phase state 551.

On system initialization, the phase state can be defined as either Stance Phase state 552 or Swing Phase state 551. Once new data is issued by the sensors (e.g., of the knee prosthetic device 1), state will be re-evaluated, and the state machine will directly transition to the correct state by comparing the sensor data to the pre-established transition conditions for stance to swing transition 554 or swing to stance transition 553. Due to the low latency required for the system to load new sensor data and the Phase state to be evaluated, there is not a hard functional limitation in having the phase considered stance or swing by default. In one non-limiting embodiment of the phase state machine, the swing to stance transition 553 is based on the comparison of the axial load applied on the lower-limb prosthetic device (e.g., of the knee prosthetic device 1) and measured by the on-board sensors with pre-defined threshold. For example, if the load cell measures an axial load superior to 8 kg, the state machine will make or identify the current state to be stance. Conversely, if the load applied on the lower-limb prosthetic device is measured to be less than 8 kg, the phase will transition to swing. A variety of sensor embodiments can be used to support the phase state machine operation. To name a few, loadcells, accelerometers, pressure sensors, displacement sensors, radar, inductive sensors, and resistive sensors can be leveraged to support the phase state machine. Additionally, stance to swing transition 554 and swing to stance transition 553 can be based on other decision mechanisms than the single thresholding comparison provided as example above. Decision making processes such as multiple thresholding or majority voting could also be applied to define the transition criteria. Additionally, the various methods for deciding if the conditions are met for allowing the system to transition from one state to the other in the phase state machine could also consider multiple data streams at the same time or use sensor integration or fusion to build a data stream containing data at a higher level of abstraction.

While the stance and swing phase are characteristic of human locomotion, they do not provide a very detailed segmentation of the behaviour required by a lower-limb prosthetic, as this phase segmentation only describes the general configuration of the lower-limb and not the behaviour of the various joints in a single phase. To achieve a level of gait control refinement as required by the end user to achieve consistent, stable, and safe locomotion, additional granularity is required, such that the actuator behaviour can also be adjusted in a more granular manner.

Figure 5B:
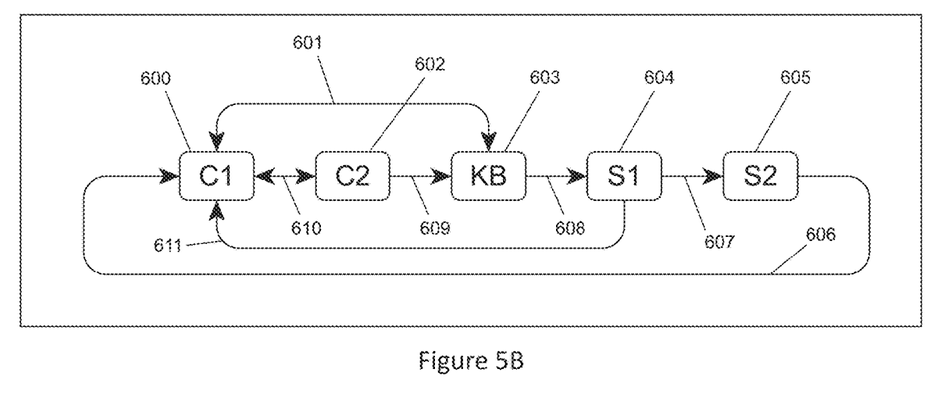
FIG. 5B is a block diagram of a sub-phase state machine.

FIG. 5B presents a subphase state machine embodiment that is particularly well suited for controlling knee prosthetic devices, such as the knee prosthetic device 1 shown in FIG. 1. While the number and the nature of the subphases can vary, the general approach is typically to consider the subphases required to properly address the requirements of the level walking activity and then to use these subphases, or a subset of them, to address the other locomotion activities, which can typically be addressed satisfactorily with a reduced number of subphases. While a lower number of subphases may make sense for devices using an actuator subsystem not allowing for refined controllability, and a higher number of subphases may increase the complexity of the control system without bringing any benefits to the overall performance, an appropriate number of subphases will allow optimal use of the actuator controllability and address the specific biomechanical requirements of the gait activity in a satisfactory manner. In the specific case of the subphase state machine presented in FIG. 5B, use of 5 subphases is aligned with the general understanding of the knee role in level walking as described in modern biomechanical analysis of the lower limb.

C1 subphase 600 represents the Contact 1 subphase of the gait cycle and consists of the level walking stance phase state starting from the occurrence of the contact of the prosthetic limb foot with the ground and where the knee is typically observed to flex under the weight of the end user. This flexion is typically observed to provide a certain level of shock absorption following the occurrence of the contact between the prosthetic foot and the ground surface. To properly support the end user weight transfer to the prosthetic limb, the prosthetic knee actuator (such as actuator 101 in FIGS. 1-2) is required to provide braking torque or torque resisting the motion imposed to the knee joint by the end user weight and momentum.

C2 subphase 602 represents the Contact 2 subphase of the gait cycle and consists in the level walking stance phase state where the knee is observed to extend, following the completion of the C1 subphase flexion motion. Extension motion occurs from a combination of the end-user forward momentum and the end-user residual limb hip extension. Proper support of the knee extension motion by the prosthetic knee actuator (such as actuator 101 in FIGS. 1-2) requires appropriate amount of resistive torque. Failure to provide enough resistive torque will let the knee quickly extend and hit the extension motion stop, which causes discomfort for the end user. On the other hand, providing too much resistive torque will slow down the extension motion and require the end user to put excessive force to extend the knee.

KB subphase 603 represents the knee break or pre-swing subphase of the level walking gait cycle and consists of the stance phase state where the knee joint is prepared to transition to swing phase. In that part of the level walking stance cycle, the user starts unloading the prosthetic limb and the residual limb thigh segment starts moving into hip flexion, after having reached maximum extension. Proper care must be directed in this subphase actuator control to allow for a smooth transition to swing, without hindering the end user hip flexion, requiring the end-user to lift himself up on his sound foot (i.e., hip-hiking) or causing the prosthetic foot to stick to the floor and breaking the forward momentum of the end-user (late stance locking). To ensure proper synchronism with the user motion and allow this last one to control the whole KB subphase, the prosthetic knee actuator (such as actuator 101 in FIGS. 1-2) is typically placed in a low resistance to motion state, which allows the end-user to properly control the knee joint behaviour in this subphase.

S1 subphase 604 represents the Swing 1 subphase of the level walking gait cycle and consists of the swing phase state where the knee joint is actively flexing while not in contact with the ground, allowing to clear the ground while the lower limb is brought back in the proper configuration for the following step. Knee flexion under the momentum imparted to the shank segment through the thigh segment acceleration requires the prosthetic knee actuator (such as actuator 101 in FIGS. 1-2) to present low resistive torque. Failure to properly leverage the residual limb momentum is typically observed to cause a slow flexion movement, which in turns is likely to cause toe-stubbing or fail at generating sufficient ground clearance while the hip is flexing the thigh segment. In both cases, end-user forward progression dynamics will be interrupted, creating a risk of fall or stumble, or reducing the overall efficiency of the walking gait pattern.

S2 subphase 605 represents the Swing 2 subphase of the level walking gait cycle and consists in the swing phase state where the knee joint is actively extending while not in contact with the ground, allowing to fully extend the knee joint in preparation for the upcoming transition to stance phase. Again in this subphase, it is required for the knee joint to achieve sufficient velocity to ensure that the limb is fully extended ahead of the moment where the prosthetic foot would contact the ground surface, while also managing the joint velocity profile in such as way as to avoid the knee from hitting the extension stop, which is uncomfortable for the user and could negatively affect the end-user's capacity to transfer weight to the prosthetic limb in a timely manner. Properly supporting the S2 subphase requires the prosthetic knee actuator (such as actuator 101 in FIGS. 1-2) to present a low resistance state for most of the subphase, followed by an increase of the actuator resistance to motion to smoothly decelerate the joint in the last part of the extension motion. This type of actuator behaviour can be obtained by using the subphase information combined with the knee position sensor data in the actuator control scheme.

C1 to C2 state transition 610 occurs when the knee joint behaviour is observed to transition from stance flexion to stance extension, under the influence of the end-user. This transition is typically triggered through monitoring of the knee joint velocity direction and typically occurs from C1 subphase 600 to C2 subphase 602 during level walking. It is possible however that transition in the opposite direction (i.e., C2 subphase 602 to C1 subphase 600) could be observed in atypical circumstances or in other activities where knee joint extension is followed by knee joint flexion while in stance phase. Interruption in the level walking stance phase gait cycle could cause the extension motion to stop and the knee to start flexing again. Similarly, sudden stopping due to the presence of an obstacle or losing balance over the prosthetic foot could also generate this type of transition. On the other hand, other activities can be managed through these subphases and provide a more visual example of the bidirectionality of this specific transition. For example, stand to sit transfer is typically supported directly through the C1 subphase 600, since the knee is flexing in stance phase. Conversely, sit to stand transfer is typically directly supported through the C2 subphase 602. Since these transfer activities can be performed in any sequence, with or without really reaching the standing and sitting end points, this illustrates the need to support this transition in a bi-directional manner.

C2 to KB state transition 609 occurs when the user is observed to be ready to initiate the transition to swing phase and is again triggered through monitoring of the embedded sensors. This corresponds to the mid-stance to late-stance part of the level walking gait cycle, where the user's center of mass is observed to have moved anteriorly to the prosthetic foot and the hip is about to start flexing. Identification of this particular configuration of the user segments and body dynamics can be achieved by making sure that the knee is in an extended position and shows low velocity, indicative that the C2 subphase 610 has really completed. Additionally, monitoring that the knee joint shows sufficient extension moment allows to estimate the end user center of mass to be located anteriorly to the prosthetic foot. Finally, monitoring that sufficient shank sagittal plane rotational velocity is observed allows to ensure that the user is actually showing forward progression momentum while rolling over the toe of the prosthetic foot and/or has started to flex the residual limb hip. As this transition is a rather dynamic one and actually requires the knee joint to be fully extended, it is typically considered as a one-way state transition. Exiting the KB state 603 to return to an earlier stance phase state in level walking requires the knee to flex, which then matches the C1 subphase 600, and not the C2 subphase 602.

KB state 603 normal exit transition pattern during level walking gait is observed to be the KB to S1 state transition 608. This transition is observed to take place when the user has completed the weight transfer to the contralateral limb, leaving the prosthetic limb now in swing phase. This transition is managed through the combination of two conditions monitored from the sensor data stream. For one, the loadcell signal has to indicate that the load on the prosthetic limb has dropped below the threshold value used to determine the phase. In other words, the phase has to be detected as being swing. Additionally, to prevent the occurrence of a false positive detection of a KB to S1 state transition 608, a minimum flexion angle is required for the state transition to be executed. In a non-limiting embodiment, an angle of 15° is used. Use of the additional minimum flexion angle condition over simply using the threshold on the loadcell measurement provides the added benefit of helping debounce the loadcell signal and makes sure the user has committed to the transition before actually implementing the state change (i.e., residual limb hip flexion has started to take place, causing the knee to flex). Debouncing is required for cases where the load transferred to the ground through the prosthetic limb would be moving across the threshold value with small amplitude, causing the system to quickly cycle through the stance and swing phases. Use of the minimum angle threshold minimizes that concern as selection of a correct threshold value allows to make sure that the user has started flexing the residual limb, which greatly removes the capacity to be loading the prosthetic limb.

KB to C1 and C1 to KB bidirectional state transition 601 integrates two specific cases that are not typically observed during level walking gait but are often encountered on the general user population based on the high variability of the environment in which human locomotion takes place, causing deviation in the normal occurrence of gait events. Firstly, C1 to KB state transition 601 is in fact equivalent to the C2 to KB state transition 609 introduced above and would typically be observed in cases where the C1 to C2 transition 610 would not be observed, mainly caused by the knee extension not taking place as per expected, but where KB transition are still observed to take place. For example, in the case where the user would enter C1 subphase 600 with a fully extended knee, the knee would not generate enough flexion torque to cause the knee to yield, or flex, under load and would not allow it to meet the conditions to enter the C2 subphase 602 from C1 subphase 600, but could still meet the conditions for the KB transition in late stance. This type of situation is often observed when users were trained to use simpler mechanical prosthetic knee technology, where they have to force the knee in hyperextension during stance phase to compensate for the device's lack of capacity to provide support.

Secondly, KB to C1 state transition 601 is required to provide a recovery mechanism to the end user and pre-empt some falls from being generated by the user falling at properly progressing through the normal gait events and subphases. Two main situations are observed in level walking where the KB to C1 transition 601 is leveraged and are both associated with a general situation where the observation of the sensor stream indicates that it would be safer for the end-user to have the knee provide support instead of the no-support joint behaviour associated with the KB state 603. In one case, this transition would be triggered by the observation of the knee extension moment being too small and the knee joint flexion angle being too large. This situation represents a case where the end-user center of mass progression has stopped while the KB state 603 was previously entered, leaving the center of mass posterior to the prosthetic foot and the end-user in an unstable position. This could be observed if the user is required to abruptly stop, or get pushed back, for example. In the other case, if the user loading of the prosthetic device is observed to increase while the KB state 603 was already entered, this is again indicative that the end-user center of mass is not progressing forward as expected and he is not transferring his weight away from the prosthetic limb like normally observed in the KB state 603.

S1 to S2 state transition 607 occurs when the knee joint has completed the level walking swing phase flexion motion and is observed to start extending. This inversion of the knee rotation direction is normally synchronized with the residual limb hip flexion motion completion and will position the lower limb in a configuration ready to support the coming prosthetic foot contact with the ground. This state transition is managed through the monitoring of the knee joint velocity direction, which is implemented through using a null velocity threshold to decide whether the current direction of motion has reached the value allowing for the transition to take place.

S1 to C1 state transition 611 is observed to occur in specific circumstances where sufficient load would be observed on the prosthetic device, through monitoring of the loadcell sensor read out, while the loadcell sensor read out is expected to be operating in swing phase. Occurrence of stance phase detection during swing flexion can be related to a variety of factors but all indicate a disruption of the normal level walking gait cycle requiring to provide support to the end-user and preventing the knee from collapsing under the user. For example, presence of an obstacle interrupting the swing flexion motion and/or interrupting the end-user forward progression momentum could easily result in this transition taking place. Obstacles such as curbs, shrubs, tall grass, or snow are typical examples of obstacles encountered in daily living. Similar to the KB to C1 case previously introduced, situations where the user would be pushed back (e.g., from pushing against a heavy door, or bumping into someone) are also cases where this transition would be observed to occur. Again, reverting to the C1 subphase 600 ensures that the knee will be providing resistance to flexion load, preventing its collapse and subsequent user fall.

S2 to C1 state transition 606 is observed to occur as the level walking swing phase extension knee joint motion completes and the prosthetic foot enters in contact with the ground again, registering load on the prosthetic limb again. Detection of the loadcell sensor signal exceeding the pre-determined threshold causes the phase to transition back to swing and the subphase to go back to the C1 subphase 600, allowing the whole cycle to start again.

Returning to FIG. 5, information provided by phase detection engine 501 is also fed to the angle-dependent torque block 504, along with the actuator position 500 information. Similarly, the angle-dependent torque 504 is a feedforward term which is fed through a gain $k_m$ 507 applied during stance phase but where the characteristic of the contribution of this arm of the controller is scaled according to the actuator position 500. Typically, but not to be considered as a limitative embodiment, this feedforward contribution is shaped like an angle-dependent torque, providing an increasing contribution over approximately the first half of the actuator motion range, before decreasing back to its original level over the second half of the actuator motion range. This contribution provides a base level actuator resistance torque which is scaled up depending on actuator angle when the prosthetic knee is operating in stance phase. This is observed to reduce the actuator performance dependency on the flexion-extension actuator velocity, which allows for more consistent support of the user's weight with increasing flexion angles and during motion direction changes, where velocity goes through a null point where the user could be left without actuator resistance while loading the actuator. Additionally, the angle-dependent torque 504 feedforward term can be defined in such a way as to compensate for the increased actuator loading from the user as the angle increases, which causes an increase in the distance between the user's upper body weight and the knee rotation axis. The velocity gain 506, static torque gain 505, and angle-dependent torque gain 507 are all summed together.

Finally, the Independent Component 508 is added to the three other arms of the controller. While the Independent Component 508 is a feedforward term like the static torque 502 or the angle-dependent torque 504, this one does not have an explicit dependency to a gait control parameter like the actuator angle 500 or the Phase 501, but instead is more heuristic in nature and accounts for specific actuator behaviors that are not properly accounted for by the three main branches of the controller structure. Typically, these behaviors are driven from specific user need and are not fundamentally part of physiological gait per se. For example, when it is found desired to maintain the knee in full extension in swing phase, the independent term is used to make the knee resistance increase to a level where the knee will remain in full extension, without any velocity term contribution. Similarly, it is found desirable to increase the actuator resistance prior to foot strike to mitigate any delays observed in ramping up the actuator resistance and user perceived knee buckling at initial loading, which is performed using the independent component 508, as velocity is also null in this case and the knee is operating in swing phase. One other example where the independent component 508 is used to directly affect the actuator behavior is in foot placement management during stairs ascent. As the knee flexion angle at foot strike is much higher in stairs ascent then in level ground or ramp ambulation, there is a need to stop the swing extension cycle to allow the user to step on the upcoming step, when climbing stairs step-over-step. When the appropriate actuator angle is reached, the high-level stairs ascent management will generate a short increase in actuator resistance in order to stop the extension motion, allowing the user to step on the flexed knee or kick-it to full extension in the case where transition back to walking is required.

The resulting sum of the four different types of contributions to the controller effort is then fed to the low-pass filter 510 block. The low-pass filter 510 characteristics are dynamically adjusted as a function of the Phase and Subphase information 511 provided by the intent management section of the control system of FIGS. 5A and 5B, allowing to achieve optimal filtering and minimal latency on actuator reaction. For example, swing phase does not show high-bandwidth set-point changes and a uniform behavior. It is then addressed with a single set of filter parameters. On the other hand, stance phase in most locomotion activities is observed to present high-bandwidth set-point changes due to the user interaction with the environment. Multiple parameter sets are then used in stance phase to ensure obtaining the optimal filter response time for all various situations. One particular low-pass filter embodiment found to be particularly suited for the task at hand is the second order Butterworth filter. While not being a limitative embodiment, this filter is known to present optimal response in the pass band with minimum latency, which is of value in the context of a real-time system.

Use of the low-pass filter on the setpoint allows getting rid of the high frequency components and smoothing out the input signal for control purposes. High-frequency components are typically generated by sensor noise, which are propagated and amplified through the different control scheme components. The high-frequency content also includes discontinuities found in the static torque (502) and angle-dependent torque (504) components of the setpoint, as well as the independent component (508). While specific considerations can be taken to minimize the discontinuous parts generated by the independent contributors to the control signal, some are unavoidable in certain scenarios and use of the low-pass filter allows uniformizing the control signal as a whole, without requiring a heuristic approach. Finally, the Luenberg-observer (503) also has a contribution to the high-frequency components since it essentially acts as a controller on the predicted and measured actuator positions with a fairly high gain. Attenuation of the aforementioned high-frequency noise and discontinuities removes audible noise generated in the actuator, contributes to attenuating possible chatter in the control loop, and provides a smoother experience to the user. Specific attention is required in compromising between having too small of a bandwidth and the delay of the filter, but the chosen design allows for minimal ringing artifacts in both the pass and stop-band, whilst still allowing for a steep drop-off.

Figure 6A:
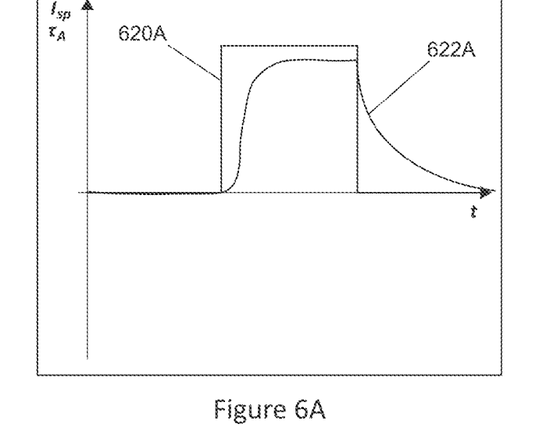
FIG. 6A illustrates a graph of a step-current applied to a shear-type MR rotary actuator and resulting resistive torque rise when the step current is applied and fall when the step current is removed, as a function of time.
Figure 6B:
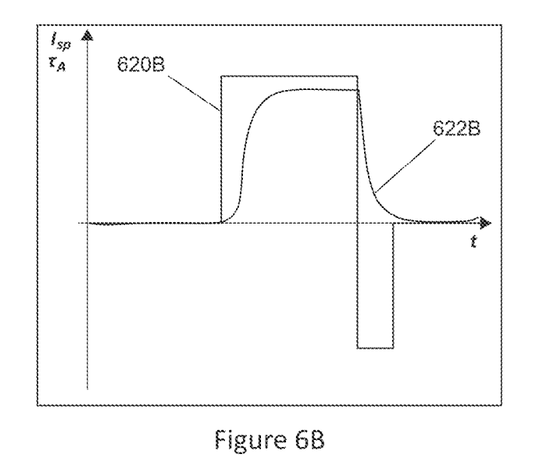
FIG. 6B illustrates a graph of a step-current applied to a shear-type MR rotary actuator and resulting resistive torque rise when the step current is applied and fall when a recovery pulse is applied to reduce resistive torque fall time.
Figure 6C:
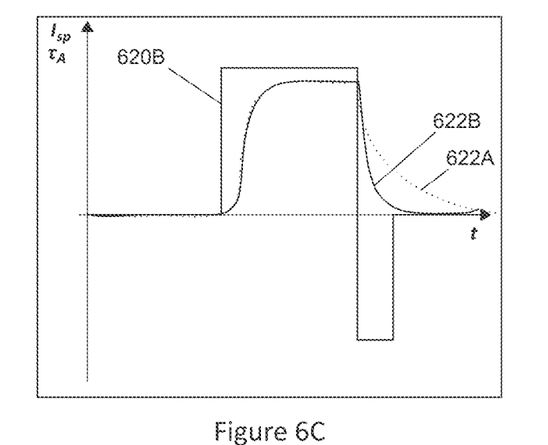
FIG. 6C illustrates a direct comparison of the graphs in FIG. 6A and FIG. 6B, illustrating the improved reduction in resistive torque fall time due to the application of the recovery pulse.

FIGS. 6A-6C present MR actuator resistive torque response characteristics for two different coil driving strategies. FIG. 6A presents the current set-point and torque response of an MR actuator being driven with a current driver that does not implement the innovative embodiment of using a recovery pulse to reduce resistive torque fall time herein described. The current set-point 620A is specified by the micro-processor and is shown plotted as a function of time (horizontal axis). For sake of simplicity, the current set-point is presented a step input, going from 0 current to a certain arbitrary current level that is defined to be less than the maximum current allowed by magnetic coil. The current level used herein is for descriptive purposes only and should not be construed as being limitative in view of the embodiment. When current rises-up in the magnetic coil and/or circuit, MR actuator resistive torque 622A is observed to ramp up at a slower rate than the current set-point, and then reach a maximum in a roughly asymptotical pattern. When the current set-point 620A is brought back to 0 again through de-activation of the magnetic coil circuit driver, it can be observed that the actuator resistive torque 622A falls at a much slower rate than it was observed on the rising edge of the current step or resistive torque activation. This phenomenon is typically observed due to the fact that there is residual magnetism present in the actuator, which takes some time to dissipate and allow the magnetic particles found in the MR fluid to regain a fully free state.

FIG. 6B shows the current set-point 620B and resistive torque 622B response of a MR actuator being driven with a current driver that does implement the inventive step herein described of using a current pulse of opposite direction to reduce resistive torque 622B fall time. Again, current set-point 620B is specified by the micro-processor and is shown plotted as a function of time (horizontal axis). Actuator resistive torque 622B response again shows a rise time significantly slower than what is observed for the current set-point. Similar to what is shown in FIG. 6A, resistive torque 622B rises at slower rate and then reaches a maximum, with an asymptotic trend. This time around, when the drive current is removed, instead of simply de-activating the H-bridge and letting the torque fall on its own, the current set-point 620B is driven for a short duration in the opposite direction, before being brought back to 0 or the current driver being de-activated. Driving the current set-point 620B in the opposite direction through the coil effectively generates a torque response 622B of similar shape and rise time as the initial one, advantageously resulting in a faster reduction of the resistive torque 622B (e.g., to a baseline resistance amount).

FIG. 6C compares the effect of the two approaches illustrated in FIG. 6A and FIG. 6B together by presenting them on the same set of axes. Again, current step 620B is presented as a step function, while resistive torque response for the system without the innovative embodiment 622A is presented by a dotted line and the resistive torque response for the system presenting the innovative embodiment 622B is presented as a solid line. From the direct comparison of the time response of the resistive torque, it can be observed that the torque response for the system presenting the innovative embodiment 622B (e.g., applying the recovery pulse of reverse direction current) drops faster to a negligible value.

Figure 7:
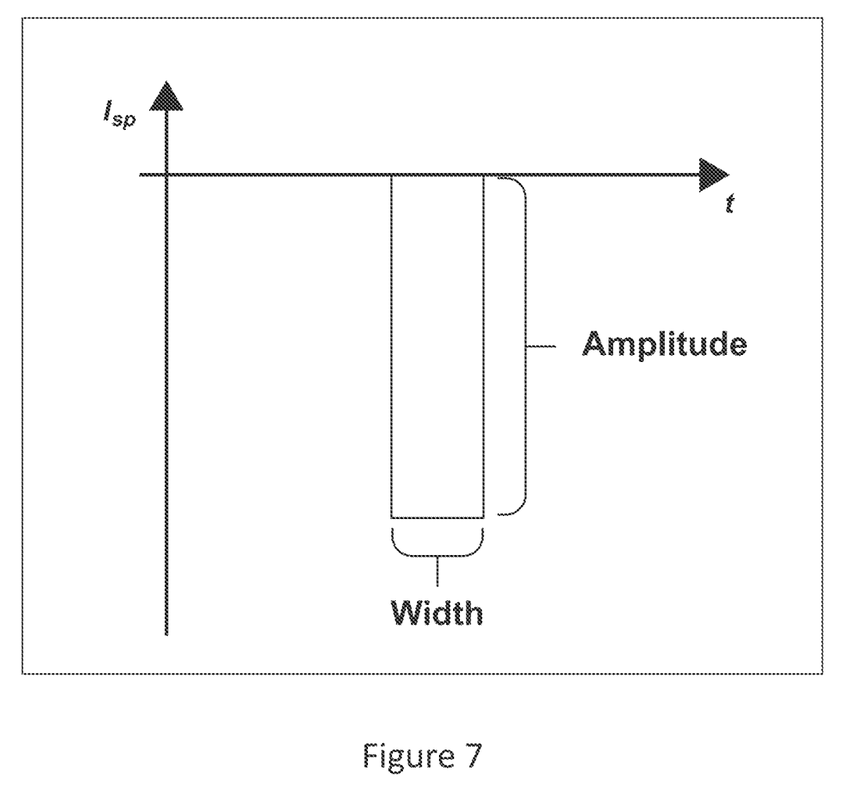
FIG. 7 is a schematic illustration of the characteristics of the recovery pulse.

FIG. 7 shows the characteristics of the recovery pulse. The width or the amplitude (or both) can be adjusted based on how much energy is trapped in the in the magnetic circuit and required to be dissipated. The width of the pulse must be greater if a low amplitude is chosen compared to a large amplitude for the same effect. As quick response is vital for this system, the width of the pulse should be as short as possible and therefore a large amplitude is chosen for a quick dissipation of the magnetic field. In one implementation, the amplitude of the reverse direction current pulse (e.g., of the recovery pulse) is equal to or greater than the amplitude of the step current input by the circuitry to the actuator to provide the resistive torque (e.g., maximum resistive torque).

While certain embodiments have been described, these embodiments have been presented by way of example only and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present disclosure is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations, one or more features from a claimed combination can, in some cases, be excised from the combination, and the combination may be claimed as a sub-combination or variation of a sub-combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Of course, the foregoing description is that of certain features, aspects and advantages of the present invention, to which various changes and modifications can be made without departing from the spirit and scope of the present invention. Moreover, the devices described herein need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or sub-combinations of these specific features and aspects of embodiments may be made and still fall within the scope of the invention. Accordingly, it should be understood that various features and aspects of the disclosed embodiments can be combined with or substituted for one another in order to form varying modes of the discussed devices.

What is claimed is:

1. A prosthetic or orthotic device, comprising:
an elongate frame configured to house electronics;
an actuator movably coupled to the elongate frame, the actuator configured to rotate in an anterior-posterior direction about a medial-lateral axis, the actuator comprising a magnetorheological (MR) fluid and a coil operable to selectively apply a magnetic field to the MR fluid to vary its viscosity and thereby vary a torsional resistance of the actuator about the medial-lateral axis; and
circuitry configured to control an amplitude and a direction of a current applied to the coil, the circuitry configured to switch a direction of current passing through the coil and to apply a reverse direction current pulse to the coil to reduce a time period over which a resistive torque of the actuator in a braking state decreases to a baseline resistance amount of the actuator in a non-braking state;
wherein the amplitude of the reverse direction current pulse is equal to or greater than an amplitude of a step current input by the circuitry to the actuator to provide the resistive torque; and
wherein one or both of an amplitude or a duration of the reverse direction current pulse is determined in part based on an approximated level of torque present in the actuator, and wherein one or both of the amplitude and the duration of the reverse direction current pulse is adjustable based on an amount of energy in the actuator required to be dissipated.

2. The prosthetic or orthotic device of claim 1, wherein the device is a prosthetic knee.

3. The prosthetic or orthotic device of claim 2, wherein said reduced period over which the resistive torque of the actuator decreases to the baseline resistance amount decreases a time period in which the prosthetic or orthotic device transitions between stance phase and swing phase.

4. The prosthetic or orthotic device of claim 3, where said transition between a stance and a swing phase of the prosthetic knee is in a stairs descent mode of ambulation.

5. The prosthetic or orthotic device of claim 1, where the actuator is coupled to a proximal portion of the elongate frame.

6. The prosthetic or orthotic device of claim 1, wherein the reverse direction current pulse has an amplitude and width configured to reduce the resistive torque to the baseline resistance amount.

7. The prosthetic or orthotic device of claim 1, wherein the circuitry includes H-bridge circuitry configured to control the amplitude and direction of the current applied to the coil.

8. A prosthetic or orthotic device, comprising:
an elongate frame configured to house electronics;
an actuator movably coupled to the elongate frame, the actuator configured to rotate in an anterior posterior direction about a medial-lateral axis, the actuator comprising a magnetorheological (MR) fluid and a coil operable to selectively apply a magnetic field to the MR fluid to vary its viscosity and thereby vary a torsional resistance of the actuator about the medial-lateral axis; and
means for actively reducing a residual magnetism in the actuator when reducing or removing the torsional resistance of the actuator based on an approximation of a level of torque present in the actuator, said means configured to apply current in an opposite direction to the coil in a pulse having an amplitude and width configured to reduce a time period over which a resistive torque decreases to a baseline resistance amount, wherein the amplitude of the pulse is equal to or greater than an amplitude of a step current input by said means to the actuator to provide the resistive torque; and
wherein one or both of the amplitude and the width of the pulse is adjustable based on an amount of energy in the actuator required to be dissipated.

9. The prosthetic or orthotic device of claim 8, wherein the prosthetic or orthotic device is a prosthetic knee.

10. The prosthetic or orthotic device of claim 9, wherein said reduced period over which the torsional resistance of the actuator decreases to the baseline resistance amount decreases a time period in which the prosthetic knee transitions between a stance phase and a swing phase.

11. The prosthetic or orthotic device of claim 10, wherein said transition between a stance phase and a swing phase of the prosthetic knee is in a stairs descent mode of ambulation.

12. The prosthetic or orthotic device of claim 8, wherein the actuator is coupled to a proximal portion of the elongate frame.

13. The prosthetic or orthotic device of claim 8, wherein the amplitude of the pulse is equal to or greater than an amplitude of a step current input by a circuitry to the actuator to provide the resistive torque.

* * * * *